(12) United States Patent
Cole

(10) Patent No.: US 7,286,882 B2
(45) Date of Patent: Oct. 23, 2007

(54) IMPLANTABLE ELECTRICAL CONNECTOR SYSTEM

(75) Inventor: Mary L. Cole, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 515 days.

(21) Appl. No.: 10/958,153

(22) Filed: Oct. 4, 2004

(65) Prior Publication Data

US 2005/0137665 A1 Jun. 23, 2005

Related U.S. Application Data

(60) Provisional application No. 60/508,558, filed on Oct. 3, 2003.

(51) Int. Cl.
*A61N 1/00* (2006.01)

(52) U.S. Cl. ..................................................... 607/116

(58) Field of Classification Search .................. 607/37, 607/116, 117, 122–132; 439/909, 948, 318, 439/332, 907
See application file for complete search history.

(56) References Cited

U.S. PATENT DOCUMENTS

| 4,402,329 | A | 9/1983 | Williams |
| 4,432,372 | A | 2/1984 | Monroe |
| 5,304,219 | A | 4/1994 | Chernoff et al. |
| 5,545,188 | A | 8/1996 | Bradshaw et al. |
| 5,575,814 | A | 11/1996 | Giele et al. |
| 5,730,628 | A | 3/1998 | Hawkins |
| 5,906,634 | A | 5/1999 | Flynn et al. |
| 6,080,188 | A | 6/2000 | Rowley et al. |
| 6,112,121 | A | 8/2000 | Paul et al. |
| 6,269,272 | B1 | 7/2001 | Fischer et al. |
| 6,575,759 | B1 | 6/2003 | Ollivier |
| 6,704,956 | B2 * | 3/2004 | Riley et al. ..................... 5/600 |
| 7,039,470 | B1 * | 5/2006 | Wessman .................... 607/122 |

* cited by examiner

*Primary Examiner*—Mark Bockelman
(74) *Attorney, Agent, or Firm*—Stephen W. Bauer; Rick L. Franzen

(57) ABSTRACT

An implantable electrical connector system, which may be used as part of an electrical lead, a connector block on an implantable pulse generator, or the connector of a lead extension. The distal most electrical contact on the proximal end of the lead (or lead extension) is adapted to provide registration or alignment of all of the electrical contacts of the proximal end of the lead (or lead extension) with electrical contacts of the distal connector of a lead extension or the electrical contacts of a connector block of an implantable pulse generator (IPG). In an exemplary embodiment, the distal most electrical contact on the proximal end portion of the lead may have a flange or shoulder that is adapted to engage the distal electrical contact of the female connection section of a lead extension or connector block. Most preferably, in this exemplary embodiment, the flange or shoulder is an integral part of the distal most electrical contact.

13 Claims, 8 Drawing Sheets

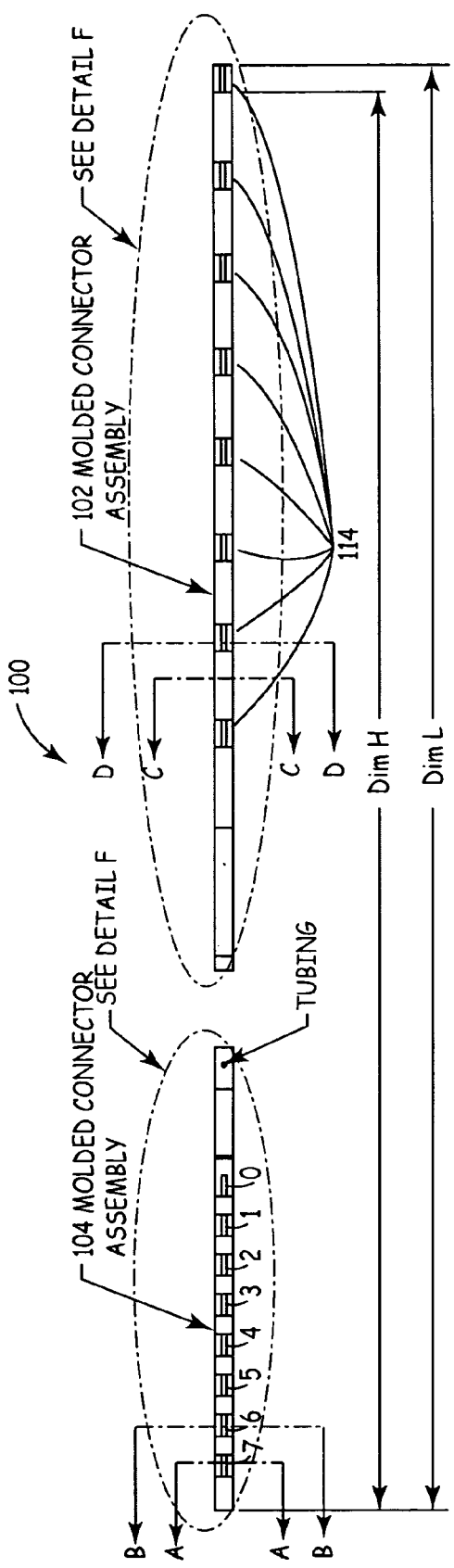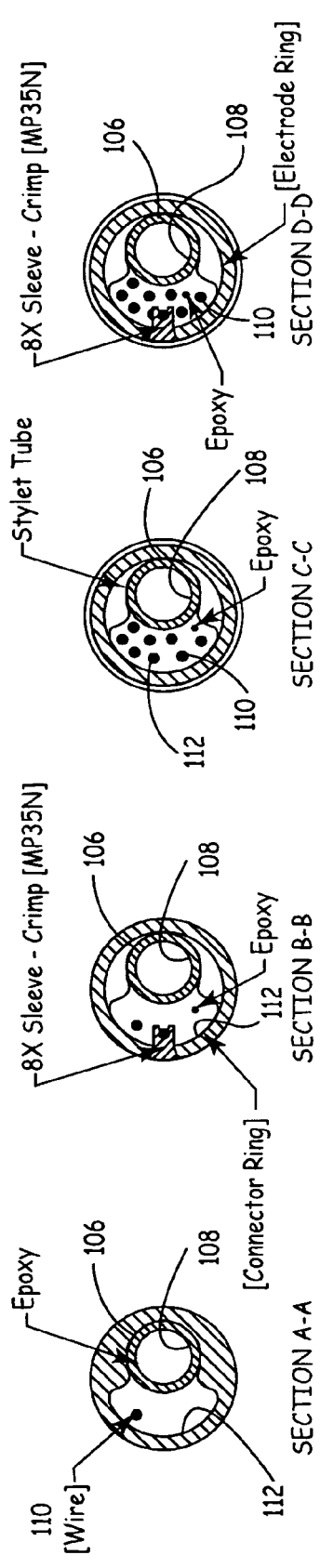

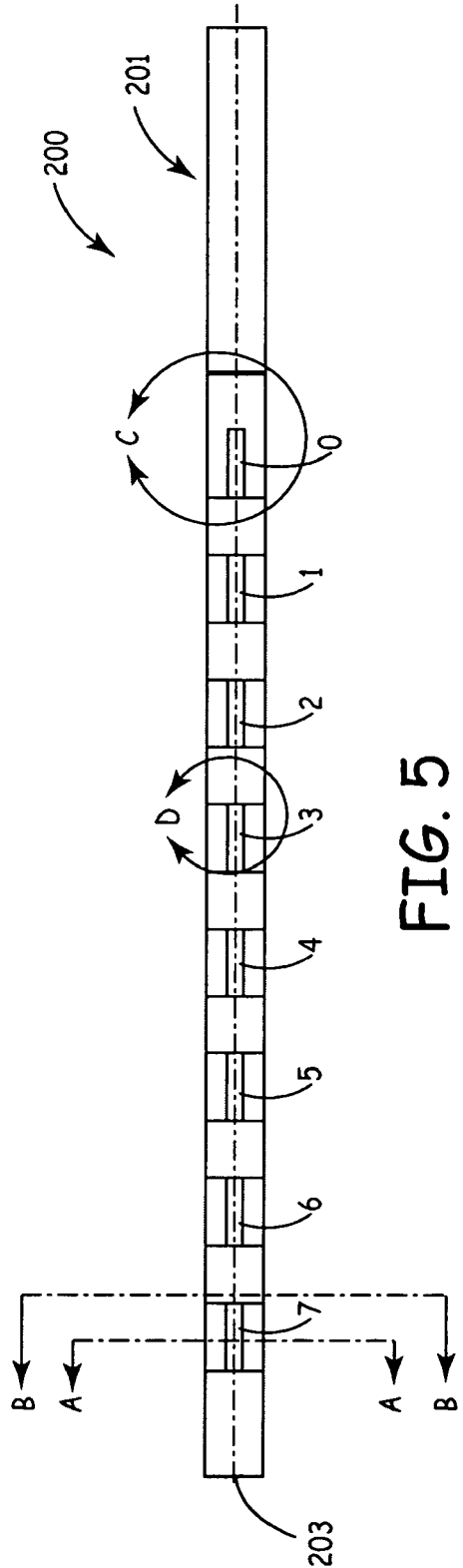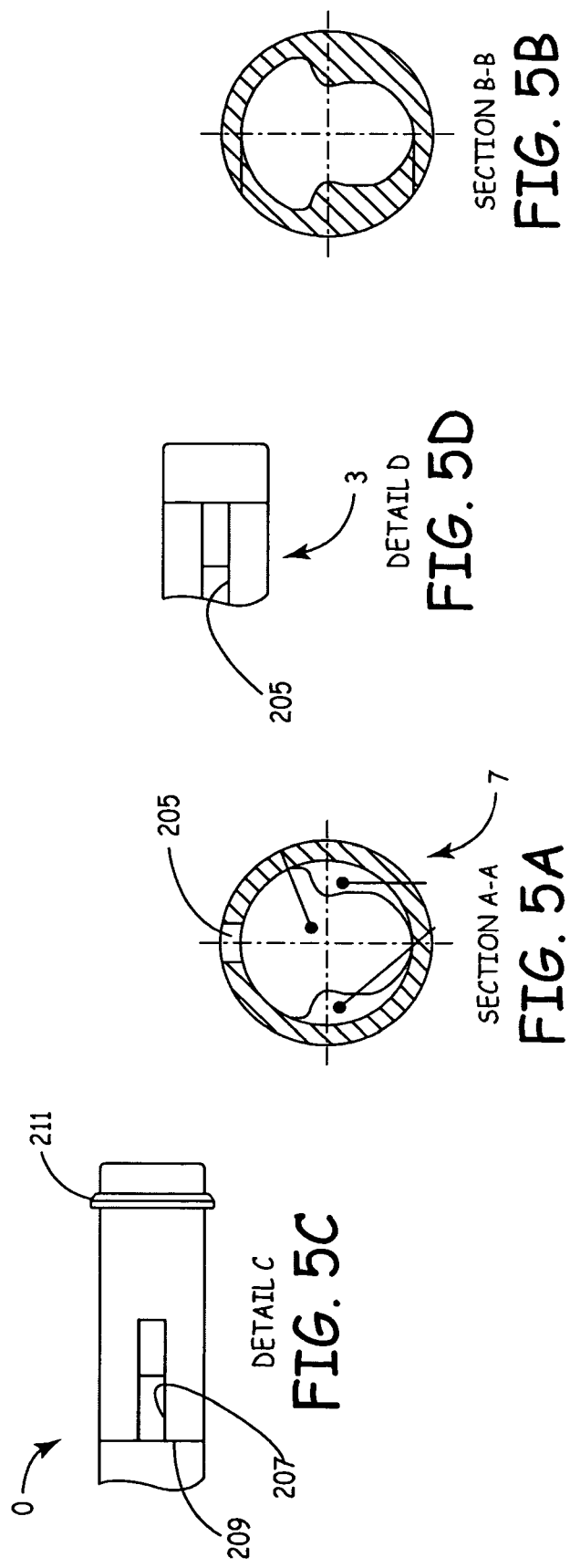
FIG. 5
FIG. 5B SECTION B-B
FIG. 5D DETAIL D
FIG. 5A SECTION A-A
FIG. 5C DETAIL C

DETAIL A

SECTION C-C

SECTION E-E

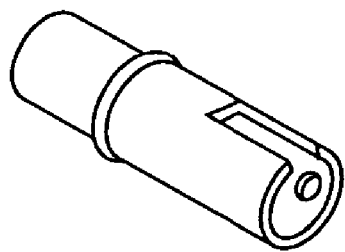
FIG. 11
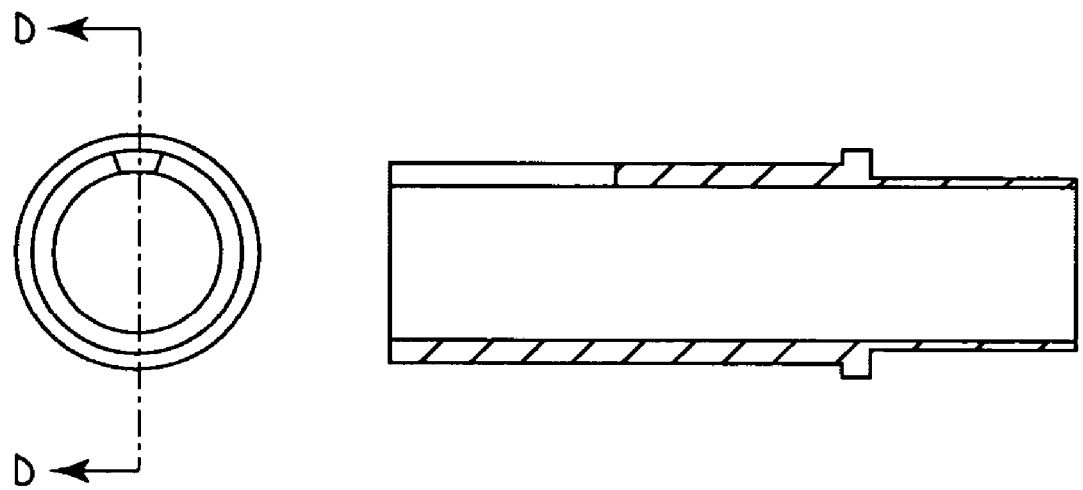
FIG. 12
FIG. 12D

IMPLANTABLE ELECTRICAL CONNECTOR SYSTEM

RELATED APPLICATIONS

This application claims priority from U.S. Provisional Application No. 60/508,558, filed Oct. 3, 2003, which is hereby incorporated herein by reference in its entirety.

FIELD

This application relates to a medical device and more particularly to implantable neurological electrical stimulators and implantable electrical stimulation leads.

BACKGROUND

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life.

One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension such as shown in Medtronic, Inc. brochure "Implantable Neurostimulation System" (1998). More specifically, the neurostimulator system can be an Itrel II™ Model 7424 or an Itrel 3™ Model 7425 available from Medtronic, Inc. in Minneapolis, Minn. that can be used to treat conditions such as pain, movement disorders and pelvic floor disorders.

The neurostimulator is typically connected to a stimulation lead that has one or more electrodes to deliver electrical stimulation to a specific location in the patient's body.

BRIEF SUMMARY OF EXEMPLARY EMBODIMENTS OF THE INVENTION

Exemplary embodiments of the invention provide system, apparatus or method for alignment of a lead connector to a mating device that works by providing a metal to metal (hard stop or click) contact to align the electrical contacts on the lead to the electrical contacts in a mating device, such as the female connector of a lead extension or the connector block of an implantable pulse generator (IPG).

Exemplary embodiments further include various combinations of a medical lead with a lead extension or implantable pulse generator (IPG), or systems comprising a medical lead, optionally a lead extension, IPG, and one or more external programmers, such as physician or patient programmers.

Exemplary embodiments of the invention use the distal most electrical contact on the proximal end of the lead (or lead extension) to provide registration or alignment of all of the electrical contacts of the proximal end of the lead (or lead extension) with electrical contacts of the distal connector of a lead extension or the electrical contacts of a connector block of an implantable pulse generator (IPG). For example, the distal most electrical contact on the proximal end portion of the lead may have a flange or shoulder that is adapted to engage the distal electrical contact of the female connection section of a lead extension or connector block. Most preferably, in this exemplary embodiment, the flange or shoulder is an integral part of the distal most electrical contact.

Among other things, exemplary embodiments of the invention allows multiple variations of lead connector sizes (e.g. four contacts) to be plugged into a contact mating device having a different number of contacts (e.g., eight contacts), and still give proper alignment of all contacts.

Exemplary embodiments also improve tolerancing stack up between connectors of leads and connectors of mating device, thus reducing probability for misalignment.

Exemplary embodiments of the invention are adapted to provide electrical communication between the distal most electrical contact on the proximal end of the lead (or lead extension) and the distal most electrical contact of the distal end of the lead extension or distal most contact of the connector block before use of optional fixation features, such as without limitation a set screw in the distal connector of a lead extension, or a set screw in a connector block).

A first exemplary embodiment of the invention is an implantable electrical lead that is adapted for connection to a female connector of an implantable pulse generator or a female connector of an implantable lead extension. The lead comprises a lead body having a proximal end portion and a distal end portion, with the distal end portion forming an inline male connector adapted for connection to the female connector. A plurality of electrodes is provided on the distal end portion. A plurality of electrical contacts is provided on the inline male connector, including a distal most electrical contact that is positioned distal of all other contacts of the plurality of electrical contacts. The distal most electrical contact has a conductive shoulder substantially facing in the proximal direction for contacting the distal most electrical contact of the female connector and registering the position of all of the plurality of electrical contacts of the inline male connector relative to the distal most electrical contact of the female connector. A conductive means is provided for electrically communicating between the plurality of electrodes and the plurality of electrical contacts.

In a second aspect of the invention, an implantable female electrical connector is provided in combination with the implantable electrical lead. The implantable female electrical connector is adapted for use in one of an implantable pulse generator and an implantable lead extension. The female electrical connector includes a bore having an opening, and a plurality of electrical contacts disposed along the bore. The plurality of electrical contacts of the female electrical connector includes a distal most electrical contact closer to the opening of the bore than all of the other electrical contacts of the female connector.

In a preferred exemplary embodiment, the distal most electrical contact of the inline male connector and the distal most electrical contact of the female connector are formed of metal providing metal to metal engagement indicating when the male connector is fully connected to the female connector.

Preferably, the plurality of electrical contacts of the inline male connector include, in addition to the distal most electrical contact, a plurality of contact rings each having an outer diameter. The distal most electrical contact of the inline male connector has a first portion having an outer diameter substantially the same as the outer diameter of the contact rings, and a second portion distal of the first portion and extending radially outwardly from the first portion to define the conductive shoulder.

The plurality of electrical contacts of the female electrical connector may comprise, in addition to the distal most electrical contact of the female electrical connector, spring-type contacts which are adapted to resiliently press against the contact rings of the male connector to make electrical contact therewith when the male connector is connected to the female electrical connector. Examples of such spring-type contacts include, for example, spring-loaded electrical contact balls, or canted coil springs.

An exemplary conductive means includes at least one conductive wire extending within the lead body between an electrode and an electrical contact. Examples include versions in which one conductive wire is provided between an electrode/contact pair, or alternative exemplary versions in which a relatively few number of electrical contacts are in electrical communication with a relatively large number of electrodes via multiples switches or the like.

BRIEF DESCRIPTION OF THE DRAWINGS

FIG. 4 shows a side view of the proximal and distal end portions of an exemplary embodiment of an implantable lead, and FIGS. 4A, 4B, 4C, and 4D show cross sectional views substantially along each of lines A-A, B-B, C-C and D-D.

FIG. 5 shows a side view of the proximal end portion of an exemplary embodiment of an implantable lead, and FIGS. 5A, 5B, 5C, and 5D show cross sectional views substantially along each of lines A-A and B-B, and exemplary details within areas C-C and D-D.

FIGS. 9A and 9B are not used in this application.

FIGS. 10A, 10C and 10D are not used in this application.

FIG. 11 is a perspective view similar to FIG. 8 of another embodiment of a contact ring having a hard stop flange.

FIG. 12 is a proximal end view of the contact ring of FIG. 11, and FIG. 12D is a cross sectional view substantially along line D-D of FIG. 12. FIGS. 12A, 12B and 12C are not used in this application.

DETAILED DESCRIPTION OF EXEMPLARY EMBODIMENTS OF THE INVENTION

Figure 1:
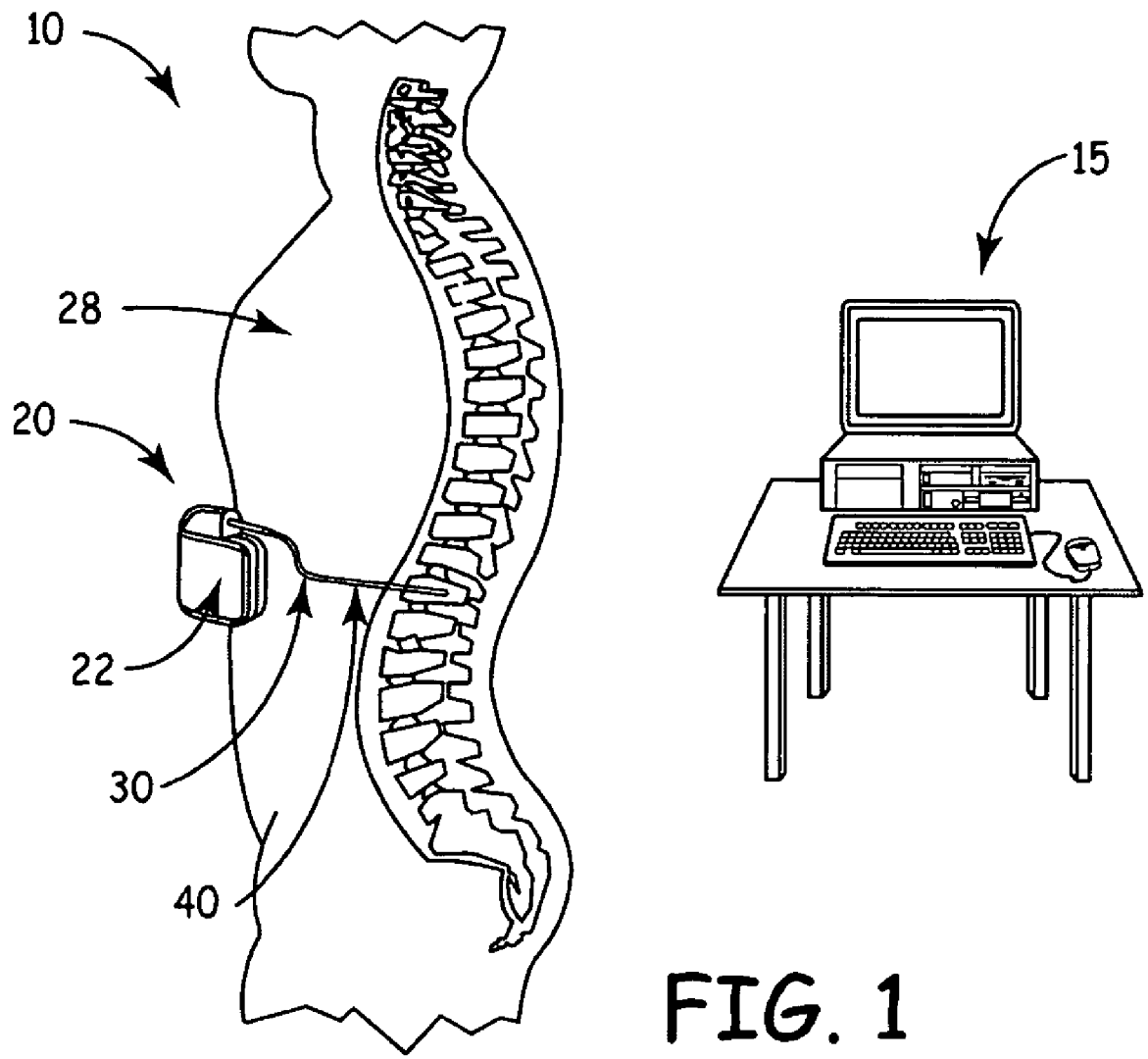
FIG. 1 shows a general environmental view for a neurostimulation system embodiment.

FIG. 1 shows a general environmental view 10 for an implantable neurostimulation system embodiment. Neurostimulation systems are used to treat conditions such as pain, movement disorders, pelvic floor disorders, gastroparesis, and a wide variety of other medical conditions. The neurostimulation system 20 includes a neurostimulator 22 such as an Itrel II® Model 7424 or an Itrel 3® Model 7425 available from Medtronic, Inc. in Minneapolis, Minn., optionally a stimulation lead extension 30, and a stimulation lead 40. The neurostimulator 22 is typically implanted subcutaneously in the patient's body 28 at a location selected by the clinician. The stimulation lead 40 is typically fixed in place near the location selected by the clinician using a device such as the adjustable anchor.

Figure 2:
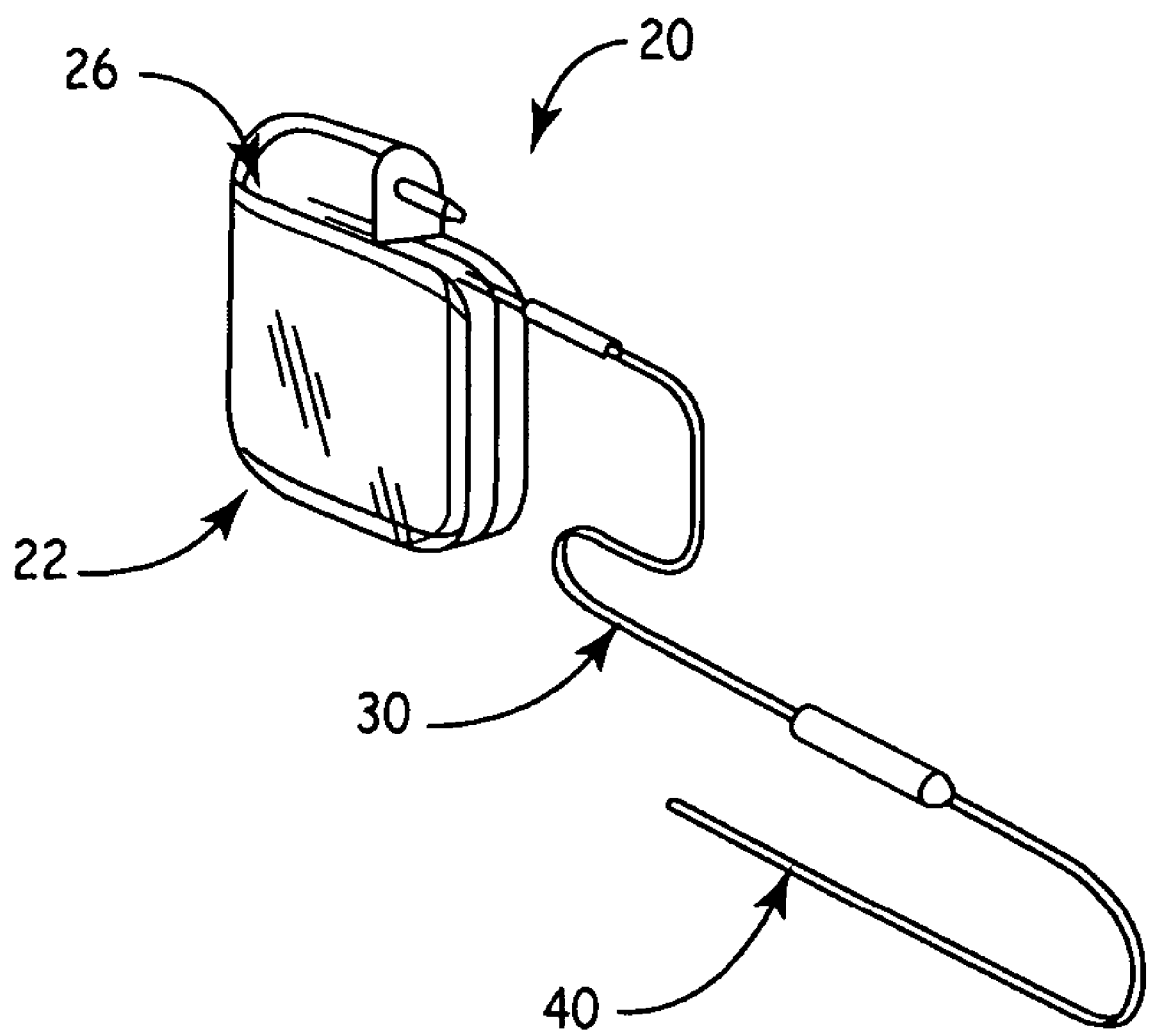
FIG. 2 shows a neurostimulation system embodiment.

FIG. 2 shows an implantable neurostimulation system 20 comprising an implantable neurostimulator 22, as stimulation lead 40, and a lead extension 30. The implantable neurostimulator 22 has a housing, a power supply carried in the housing 24, and stimulation electronics coupled to the battery and coupled to a connector block 26, which is also known as a terminal block. The stimulation lead 40 has a lead proximal end 45, a lead distal end 41 and a lead body 43. The lead proximal end 45 has at least one electrical connector 46 (also known as electrical terminals) and the lead distal end 41 has at least one stimulation electrode 42. There is at least one lead conductor 44 contained in the lead body 43 that is electrically connecting the electrical connector 46 to the stimulation electrode 42.

An implantable neurological low polarization stimulation or monitoring system comprises an implantable neurological stimulator 22 or neurological monitor, an implantable neurological lead 40, and at least one electrode 42, although as illustrated in FIGS. 4 and 5 additional electrodes, such as eight electrodes, are preferred in the exemplary embodiments of those figures. The implantable neurological stimulator 22 can be a Medtronic Itrel II® Model 7424 or an Itrel 3® Model 7425 or the like, both of which are commercially available. The neurological monitor 15 can be a Medtronic Neurodiagnostics Keypoint monitoring system.

The implantable neurological lead 40 comprises a lead proximal end 45, a lead distal end 41, at least one conductor 44, at least on low polarizing electrode 42, and at least one electrical connector 46. The lead proximal end 45 contains at least one electrical connector 46 that couples to the implantable neurological stimulator 22 or neurological monitor. The lead distal end 41 contains at least one low polarizing electrode 42. The conductor 44 contained in the lead 40 extending from the lead proximal end 45 to the lead distal end 41, the conductor 44 being electrically insulated by a polymer. The polymer could be, but is not limited to, ethylene tetrafluoroethylene (ETFE), polytetrafluoroethylene (PTFE), silicone rubber or polyurethane. Other materials that act as electrical insulators can be used. The electrical connector 46 is carried on the lead proximal end 45 and electrically connected to the conductor 44. The neurological lead 40 can be configured as a neurological stimulation lead, a neurological sensing lead, and a combination of both as a neurological stimulation and sensing lead.

Figure 3:
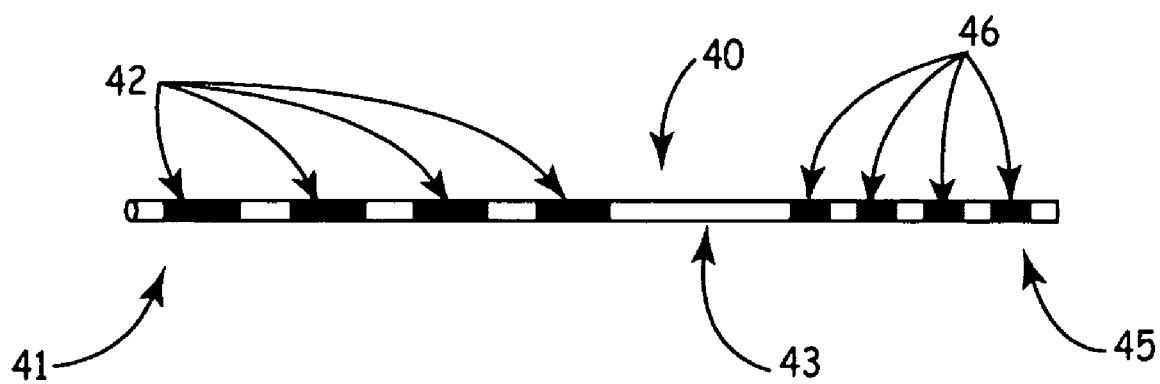
FIG. 3 shows a neurostimulation lead embodiment.

FIGS. 3 shows an implantable neurostimulation lead 40 embodiments that have a lead proximal end 45, a lead distal end 41 and a lead body 43. The lead proximal end 45 has at least one electrical contact 46 for connecting to a lead extension 30 or neurostimulator connector block 26. The lead distal end 41 has at least one stimulation electrode 42.

The lead body 43 carries at least one conductor 44 electrically connecting the lead proximal electrical contact 46 with the lead distal end 41 stimulation electrode 42.

The lead body 43 can be composed of a wide variety of materials and configurations. Materials may include, but not be limited to silicone rubber, polyurethane, fluoropolymers and the like. Configurations could include monolumen and multilumen tubings. The conductor 44 that electrical connects the lead proximal end 45 electrical contact 46 with the lead distal end 41 stimulation electrode 42 can be composed of a wide variety of material and configurations. Materials may include, but not be limited to MP35N, silver drawn filled tubing (Ag-DFT), Platinum iridium alloys, platinum and the like. Configurations could include stranded, braided or solid wire configured in linear or helical coil arrangements.

Figure 6:
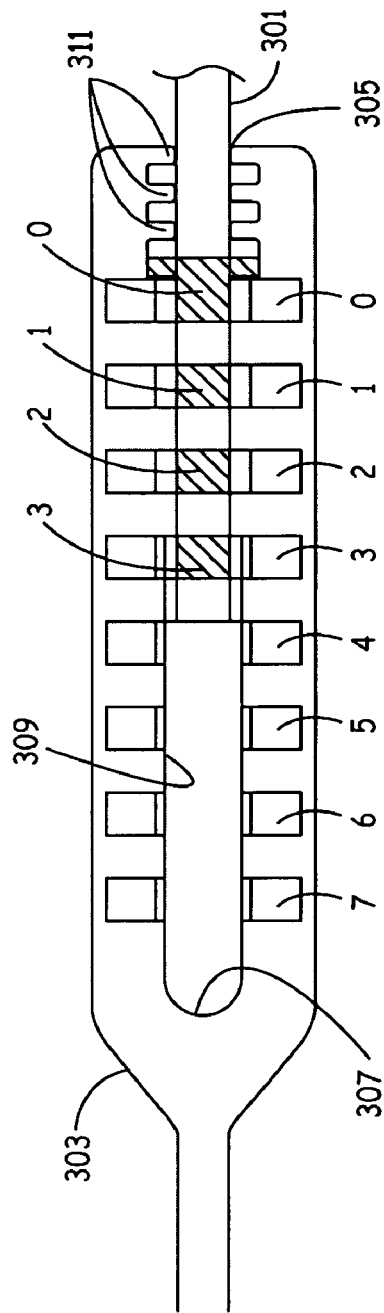
FIG. 6 is a hybrid view in which a longitudinal cross sectional view through exemplary embodiments of a connector portion of an extension having eight electrical contacts, and a side view of a proximal end portion of a lead having four electrical contacts, are shown.

FIG. 4 illustrates further details of a preferred exemplary lead 100 having a molded distal electrode assembly 102 and molded proximal connector assembly 104. As used herein, the proximal refers to the direction toward other components of the implantable system, such as the connector of an extension set or the connector block of an IPG, and distal refers to the direction away from these components. In FIGS. 5 and 6, for purposes of illustration only, the proximal direction is toward the right side of the sheet and the distal direction is toward the left side of the sheet.

FIGS. 4A-4C are cross sectional views that reveal various exemplary details of an exemplary lead 100. For example, these illustrate use of a stylet guide tube 106 having a stylet guide lumen 108. The stylet guide tube 106 is received, along with conductors 110, within a main lumen 112.

As illustrated in FIG. 5, the electrical contacts of the proximal end portion 201 of lead 200 may be identified, for example, as contact 0, 1, 2, 3, 4, 5, 6, 7. The convention employed herein is to start numbering from zero starting with the distal most contact (e.g., 0) of the proximal end 201 and going contact-by-contact toward the proximal end 203. This convention will also be adhered to herein with respect to the contacts (also 0-7) of the mating device, such as illustrated in FIG. 6. In the case of the mating device 303, the convention may also be understood as starting at zero from the opening 305 and counting up toward the blind end 307 of the lead-receiving passageway 309.

FIG. 5A illustrates exemplary details of contact 7, and FIG. 5D illustrates exemplary details of contact 3, but these exemplary details may be generalized in exemplary embodiments to contacts 1-7.

These contacts 0-7 are preferably in the form of an electrically conductive contact ring having a slot 205 for receipt of a connector on a respective conductor wire, such as a fitting on a crimp connector. In preferred exemplary embodiments the conductors are attached in this way to both of the electrodes, e.g., electrodes 114 illustrated in FIG. 4, and the contacts, e.g., contacts 0-7 illustrated in FIG. 5 or their counterparts in FIG. 4. Other connections between conductor and contact ring may alternatively be employed, such as welding, conductive adhesives, interference fit, or combinations thereof, but will not be detailed herein.

The slot 205 is shown in the exemplary embodiment as extending across the length, or axial direction, of the contact ring 1-7 but it will be understood that the slot could extend only part way across the contact ring. As used herein, the term "length" of contact ring 1-7 has been used for the dimension of contact ring 1-7 corresponding to the longitudinal direction of the lead 200.

FIG. 5C illustrates exemplary details of a preferred exemplary distal most contact 0 of the proximal connection portion 201 of the lead 200. Contact 0 includes a slot 207 that preferably extends from the proximal end 209 of the contact ring 0 only part way across the length of the contact ring 0. Again, the term "length" has been used for the dimension of contact ring 0 corresponding to the longitudinal direction of the lead 200. Slot 207 is employed for the same basic use as slot 205 of contacts 1-7.

Contact 0 further includes a flange 211 that preferably provides a metal to metal (hard stop or click) engagement with the end of the electrical contact of the female connector of a lead extension or connector block of an IPG to align the electrical contacts on the lead to the electrical contacts in a mating device, such as the connector of a lead extension or the connector block of an implantable pulse generator (IPG). The distal most electrical contact 0 on the proximal end portion 201 of the lead 200 (or lead extension) to provide registration or alignment of all of the electrical contacts 0-7 of the proximal end portion 201 of the lead 200 (or lead extension) with electrical contacts of the distal connector of a lead extension or the electrical contacts of a connector block of an implantable pulse generator (IPG).

It may be seen how in this exemplary embodiment, contact 0 is also adapted to provide electrical communication between the distal most electrical contact on the proximal end of the lead (or lead extension) and the distal most electrical contact of the distal end of the lead extension or distal most contact of the connector block before use of optional fixation features, such as without limitation a set screw in the distal connector of a lead extension, or a set screw in a connector block). In particular the flange 211 may preferably be formed as one integral conductive piece of the contact ring 0 such that electrical contact is made between at least the flange and the corresponding contact on the mating device, and thus the conductor and electrode corresponding to contact ring 0 are brought into electrical communication with the mating device.

FIG. 6 illustrates, among other things, how the flanged distal contact 0 of the proximal end 301 of the lead 300 facilitates the use of multiple variations of lead connector sizes (e.g. four contacts 0-4 as illustrated) to be plugged into a contact mating device 303 (e.g., distal connector of a lead extension or connector block of an IPG) having a different number of contacts (e.g., eight contacts 0-7 as illustrated), and still give proper alignment of all contacts. It will be understood that this would allow other variations, such as without limitation one versus four, . . . , two versus four, . . . , two versus eight, three versus, eight, . . . , eight versus sixteen, . . . , etc.

The contacts 1-7 of the mating device 303 may be in the form of spring-type contacts, such as without limitation spring-loaded electrical contact balls, or canted coil springs such as available under the trade designation "BalContact springs" from Bal Seal Engineering Inc., Foothill Ranch, Calif. A exemplary canted-coil spring is a round-wire spring with inclining (canted), elliptical coils that deflect when compressed. Contact 0 of the mating device 303 preferably includes a set screw or other manually activated mechanism. Of course, it will be understood that this description of the mating device 303 is for purposes of illustration only and any suitable mechanism or technique for providing electrical communication between the contacts 0-7 of the mating device and the contacts, e.g., 0-3 or 0-7, of the proximal connection end portion of the lead 301 or lead extension may be employed.

The mating device 303 may have a seal or plurality of seals 311 that sealingly engage the lead 300. The seals 311 are preferably formed of elastomeric material.

Figure 7:
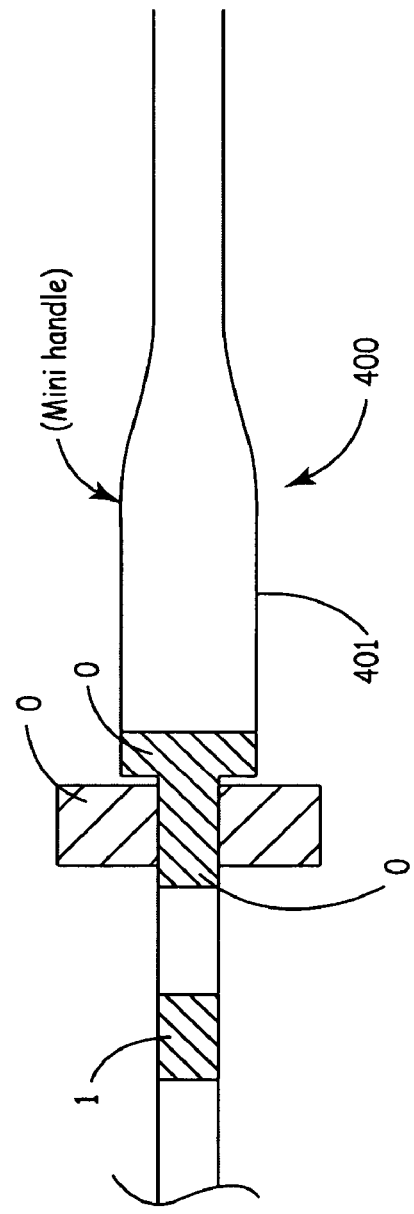
FIG. 7 is longitudinal cross sectional view through another exemplary embodiment of part of a proximal end of a lead having a shoulder engaging a contact on the connector of an extension set or connector block of an implantable pulse generator.
Figure 8:
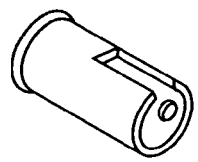
FIG. 8 is a perspective view of an exemplary embodiment of a contact ring having a hard stop flange.
Figure 10:
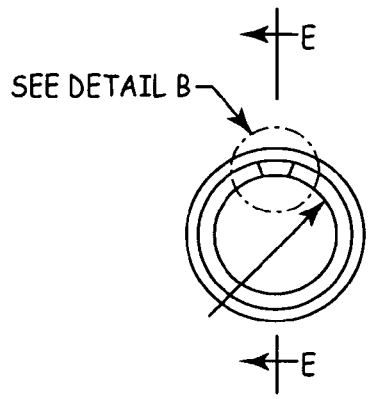
FIG. 10 is a proximal end view of the contact ring of FIGS. 8, 9 and 9C.
Figure 9:
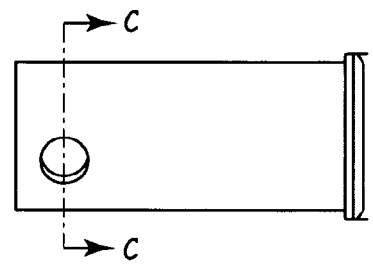
FIG. 9 is a side view of the contact ring of FIG. 8.
Figure 10B:
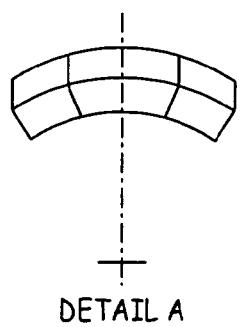
FIG. 10B is a detailed view of a part thereof.
Figure 9C:
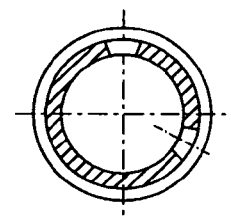
FIG. 9C is a cross sectional view substantially along line C-C of FIG. 9.
Figure 10E:
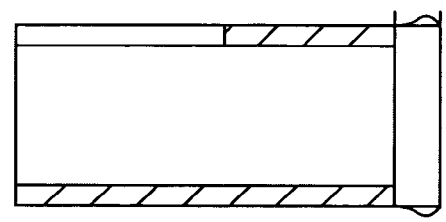
FIG. 10E is a cross sectional view substantially along line E-E of FIG. 10.

FIG. 7 illustrates an embodiment in which the lead 400 includes a thickened section 401 adjacent contact ring 0 to provide a mini-handle and optionally some additional stiffness to the portion of the lead 400 immediately proximate the mating device, the distal most contact of which is also designated 0.

Exemplary embodiments may be used for any implantable tissue stimulation, such as spinal cord stimulation, brain stimulation, sacral nerve stimulation, vagal nerve stimulation, peripheral nerve stimulation, cardiac stimulation, etc.

Thus, embodiments of the implantable medical lead and method of manufacture are disclosed. One skilled in the art will appreciate that the present invention can be practiced with embodiments other than those disclosed. The disclosed embodiments are presented for purposes of illustration and not limitation.

What is claimed is:

1. An implantable electrical lead adapted for connection to a female connector of an implantable pulse generator or a female connector of an implantable lead extension, the female connector having a plurality of electrical contacts disposed along a bore having an opening, the plurality of electrical contacts including a distal most electrical contact closer to the opening of the bore than all of the other electrical contacts of the female connector, the lead comprising:

a lead body having a proximal end portion and a distal end portion, the distal end portion forming an inline male connector adapted for connection to the female connector;

a plurality of electrodes on the distal end portion;

a plurality of electrical contacts on the inline male connector, including a distal most electrical contact that is positioned distal of all other contacts of the plurality of electrical contacts, the distal most electrical contact having a conductive shoulder substantially facing in the proximal direction for contacting the distal most electrical contact of the female connector and registering the position of all of the plurality of electrical contacts of the inline male connector relative to the distal most electrical contact of the female connector, the plurality of electrical contacts of the inline male connector including, in addition to the distal most electrical contact, a plurality of contact rings each having an outer diameter, the distal most electrical contact of the inline male connector having a first portion having an outer diameter substantially the same as the outer diameter of the contact rings, and a second portion distal of the first portion and extending radially outwardly from the first portion to define the conductive shoulder; and conductive means for electrically communicating between the plurality of electrodes and the plurality of electrical contacts.

2. The implantable electrical lead of claim 1 wherein the conductive means includes at least one conductive wire extending within the lead body between an electrode and an electrical contact.

3. A combination of:

an implantable female electrical connector adapted for use in one of an implantable pulse generator and an implantable lead extension, the female electrical connector including:

a bore having an opening; and a plurality of electrical contacts disposed along the bore, the plurality of electrical contacts including a distal most electrical contact closer to the opening of the bore than all of the other electrical contacts of the female connector; and an implantable electrical lead comprising:

a lead body having a proximal end portion and a distal end portion, the distal end portion forming an inline male connector adapted for connection to the female connector;

a plurality of electrodes on the distal end portion;

a plurality of electrical contacts on the inline male connector, including a distal most electrical contact that is positioned distal of all other contacts of the plurality of electrical contacts of the inline male connector, the distal most electrical contact of the male inline connector having a conductive shoulder substantially facing in the proximal direction for contacting the distal most electrical contact of the female connector and registering the position of all of the plurality of electrical contacts of the inline male connector relative to the distal most electrical contact of the female connector; and conductive means for electrically communicating between the plurality of electrodes and the plurality of electrical contacts.

4. The combination of claim 3 wherein the plurality of electrical contacts of the inline male connector include, in addition to the distal most electrical contact, a plurality of contact rings each having an outer diameter, the distal most electrical contact of the inline male connector having a first portion having an outer diameter substantially the same as the outer diameter of the contact rings, and a second portion distal of the first portion and extending radially outwardly from the first portion to define the conductive shoulder.

5. The combination of claim 4 wherein the plurality of electrical contacts of the female electrical connector comprise, in addition to the distal most electrical contact of the female electrical connector, spring-type contacts which are adapted to resiliently press against the contact rings of the male connector to make electrical contact therewith when the male connector is connected to the female electrical connector.

6. The combination of claim 5 wherein the spring-type contacts comprise contacts selected from the group consisting of spring-loaded electrical contact balls, or canted coil springs.

7. The combination of claim 6 wherein the conductive means includes at least one conductive wire extending within the lead body between an electrode and an electrical contact.

8. The combination of claim 3 wherein the distal most electrical contact of the inline male connector and the distal most electrical contact of the female connector are formed of metal providing metal to metal engagement indicating when the male connector is fully connected to the female connector.

9. An implantable connector system for use to connect in electrical communication at least two of an implantable pulse generator, an implantable lead extension or an implantable electrical lead, the connector system comprising:

an implantable female electrical connector including:

a bore having an opening defining the distal end of the bore; and a plurality of electrical contacts disposed along the bore, the plurality of electrical contacts including a distal most electrical contact closer to the opening of the bore than all of the other electrical contacts of the female connector; and an implantable electrical inline male connector adapted for connection to the female connector, the electrical inline male connector being elongate and having a proximal end, the male connector including:

a plurality of electrical contacts on the inline male connector, including a distal most electrical contact that is positioned distal of all other contacts of the plurality of electrical contacts of the inline male connector, the distal most electrical contact of the male inline connector having a conductive shoulder substantially facing in the proximal direction for contacting the distal most electrical contact of the female connector and registering the position of all of the plurality of electrical contacts of the inline male connector relative to the distal most electrical contact of the female connector.

10. The implantable connector system of claim 9 wherein the distal most electrical contact of the inline male connector and the distal most electrical contact of the female connector are formed of metal providing metal to metal engagement indicating when the male connector is fully connected to the female connector.

11. The implantable connector system of claim 10 wherein the plurality of electrical contacts of the inline male connector include, in addition to the distal most electrical contact, a plurality of contact rings each having an outer diameter, the distal most electrical contact of the inline male connector having a first portion having an outer diameter substantially the same as the outer diameter of the contact rings, and a second portion distal of the first portion and extending radially outwardly from the first portion to define the conductive shoulder.

12. The implantable connector system of claim 11 wherein the plurality of electrical contacts of the female electrical connector comprise, in addition to the distal most electrical contact of the female electrical connector, spring-type contacts which are adapted to resiliently press against the contact rings of the male connector to make electrical contact therewith when the male connector is connected to the female electrical connector.

13. The implantable connector system of claim 12 wherein the spring-type contacts comprise contacts selected from the group consisting of spring-loaded electrical contact balls, or canted coil springs.

* * * * *